US007912528B2

(12) United States Patent
Krishnan et al.

(10) Patent No.: US 7,912,528 B2
(45) Date of Patent: Mar. 22, 2011

(54) SYSTEMS AND METHODS FOR AUTOMATED DIAGNOSIS AND DECISION SUPPORT FOR HEART RELATED DISEASES AND CONDITIONS

(75) Inventors: Sriram Krishnan, Exton, PA (US); Alok Gupta, Bryn Mawr, PA (US); R. Bharat Rao, Berwyn, PA (US); Dorin Comaniciu, Princeton Jct., NJ (US); Xiang Sean Zhou, Plainsboro, NJ (US)

(73) Assignees: Siemens Medical Solutions USA, Inc., Malvern, PA (US); Siemens Corporation, Iselin, NJ (US)

( * ) Notice: Subject to any disclaimer, the term of this patent is extended or adjusted under 35 U.S.C. 154(b) by 1198 days.

(21) Appl. No.: 10/876,801

(22) Filed: Jun. 25, 2004

(65) Prior Publication Data

US 2005/0020903 A1  Jan. 27, 2005

Related U.S. Application Data

(60) Provisional application No. 60/482,327, filed on Jun. 25, 2003, provisional application No. 60/482,293, filed on Jun. 25, 2003, provisional application No. 60/541,360, filed on Feb. 3, 2004.

(51) Int. Cl.
*A61B 5/05* (2006.01)
(52) U.S. Cl. ........................................ 600/407; 382/128
(58) Field of Classification Search ........... 600/407–480
See application file for complete search history.

(56) References Cited

U.S. PATENT DOCUMENTS 6,021,404 A * 2/2000 Moukheibir ..................... 706/46
6,028,956 A * 2/2000 Shustorovich et al. ........ 382/156
6,099,469 A * 8/2000 Armstrong et al. ........... 600/300
6,247,004 B1   6/2001 Moukheibir
6,248,063 B1 * 6/2001 Barnhill et al. ............... 600/300
(Continued)

FOREIGN PATENT DOCUMENTS

JP       2003 325458 A    11/2003
WO       WO 01/26026 A2   4/2001

OTHER PUBLICATIONS

International Search Report including Notification of Transmittal of the International Search Report, International Search Report, and Written Opinion of the International Searching Authority.

(Continued)

*Primary Examiner* — Brian Casler
*Assistant Examiner* — Nasir Shahrestani
(74) *Attorney, Agent, or Firm* — Peter Withstandley

(57) ABSTRACT

CAD (computer-aided diagnosis) systems and applications for cardiac imaging are provided, which implement methods to automatically extract and analyze features from a collection of patient information (including image data and/or non-image data) of a subject patient, to provide decision support for various aspects of physician workflow including, for example, automated assessment of regional myocardial function through wall motion analysis, automated diagnosis of heart diseases and conditions such as cardiomyopathy, coronary artery disease and other heart-related medical conditions, and other automated decision support functions. The CAD systems implement machine-learning techniques that use a set of training data obtained (learned) from a database of labeled patient cases in one or more relevant clinical domains and/or expert interpretations of such data to enable the CAD systems to "learn" to analyze patient data and make proper diagnostic assessments and decisions for assisting physician workflow.

38 Claims, 6 Drawing Sheets

U.S. PATENT DOCUMENTS

| | | | |
|---|---|---|---|
| 6,674,879 B1* | 1/2004 | Weisman et al. | 382/128 |
| 7,043,063 B1* | 5/2006 | Noble et al. | 382/128 |
| 2003/0191666 A1* | 10/2003 | Kline | 705/2 |

OTHER PUBLICATIONS

Lindahl et al., "Automated Interpretation of Myocardial Perfusion Scintigrams Using Artificial Neural Networks", European Association of Nuclear Medicine, Copenhagen 1996.

Edenbrandt et al., "Physicians Interpreting Myocardial Scintigrams Benefit From the Advice of Neural Networks", European Association of Nuclear Medicine, Glasgow 1997.

Lindahl et al., "Automated Interpretation of Myocardial SPECT Perfusion Images Using Artificial Neural Networks", J. Nucl Med. 38(12), pp. 1870-1875, 1997.

Lindahl et al., "Scintigraphic Diagnosis of Coronary Artery Disease: Myocardial Bull's-Eye Images Contain the Important Information", Clin Physiol.. 18(6), pp. 554-561, 1998.

Järund et al., "Web-based Interpretation of Myocardial Perfusion Images", European Association of Nuclear Medicine, Barcelona 1999.

Lindahl et al., "Improved Classifications of Myocardial Bull's-Eye Scintigrams with Computer-Based Decision Support System", J Nucl Med 40(1), pp. 96-101, 1999.

Lindahl et al., "Myocardial SPET: Artificial Neural Networks Describe Extent and Severity of Perfusion Defects", Clin Physiol. 19(6), pp. 497-503, 1999.

Ohlsson et al., "WWW based service for automated interpretation of diagnostic Images: the AIDI-Heart project", Proc High-Performance Computing and Networking, pp. 941-950, 1999.

Järund et al., "Internet based artificial neural networks for the interpretation of medical images", Proc. Artificial Neural Networks in Medicine and Biology, pp. 87-92, 2000.

Lindahl et al., "Scandinavian test of artificial neural network for classification of myocardial perfusion images", Clini Physiol. 20(4), pp. 253-261, 2000.

Toft et al., "The optimal reference population for cardiac normality in myocardial SPET in the detection of coronary artery stenoses: patients with normal coronary angiography or subjects with low likelihood of coronary artery disease", Eur J Nucl Med. 28(7), pp. 831-835, 2001.

Haraldsson et al., "Value of exercise data for the interpretation of myocardial perfusion SPECT", J Nucl Cardiol. 9(2), pp. 169-173, 2002.

Japanese Office Action (including translation) for Application No. 2006-552106 dated Dec. 7, 2010.

* cited by examiner

SYSTEMS AND METHODS FOR AUTOMATED DIAGNOSIS AND DECISION SUPPORT FOR HEART RELATED DISEASES AND CONDITIONS

CROSS-REFERENCE TO RELATED APPLICATIONS

This application claims priority to U.S. Provisional Application Ser. No. 60/482,327, filed on Jun. 25, 2003, and to U.S. Provisional Application Ser. No. 60/482,293, filed on Jun. 25, 2003, and to U.S. Provisional Application Ser. No. 60/541,360, filed on Feb. 3, 2004, which are all fully incorporated herein by reference.

TECHNICAL FIELD OF THE INVENTION

The present invention relates generally to systems and methods for providing automated diagnosis and decision support for medical imaging and in particular, to CAD (computer-aided diagnosis) systems and applications for cardiac imaging, which implement machine-learning techniques to enable automated diagnosis of heart diseases and conditions such as cardiomyopathy, coronary artery disease and other heart-related medical conditions, automated assessment of regional myocardial function through wall motion analysis, and other automated decision support functions to assist physician workflow.

BACKGROUND

Coronary artery disease and other heart-related diseases are very prevalent, especially in western civilizations, and lead to the death of many people each year. By detecting heart related diseases as early as possible, appropriate, effective and cost-effective treatment can be implemented to reduce fatality. In the field of cardiology, various systems and techniques are used for accurate and early detection of heart disease.

For instance, angiography is one method that can be used for directly measuring coronary occlusion (i.e., blockage of the coronary arteries due to calcification). However, these measurements often require invasive procedures. Furthermore, although angiography can be used to identify and measure occlusions, such methods cannot measure or otherwise assess the effects of such occlusions. Indeed, the effect of coronary occlusion is typically manifested regionally within the heart wall, resulting in abnormalities of myocardial tissue or myocardial function. For instance, infarction is a condition that refers to the development of an area of dead or dying myocardial tissue (infarct) due to inadequate blood flow through the coronary vessels that normally supply blood to the myocardial tissue.

Typically, methods for assessing myocardial function are performed by analyzing wall motion through cardiac imaging to identify wall motion abnormalities. In general, in the field of medical imaging, various imaging modalities and systems can be used for generating medical images of anatomical structures of individuals for screening and evaluating medical conditions. These imaging systems include, for example, CT (computed tomography) imaging, MRI (magnetic resonance imaging), NM (nuclear magnetic) resonance imaging, X-ray systems, US (ultrasound) systems, PET (positron emission tomography) systems, etc. Each imaging modality may provide unique advantages over other modalities for screening and evaluating certain types of diseases, medical conditions or anatomical abnormalities, including, for example, cardiomyopathy, colonic polyps, aneurisms, lung nodules, calcification on heart or artery tissue, cancer micro calcifications or masses in breast tissue, and various other lesions or abnormalities.

Due to its availability, relative low cost, and noninvasiveness, cardiac ultrasound is an imaging modality that is typically used for performing wall motion analysis for purposes of assessing cardiac functions (e.g., assessing regional systolic wall motion abnormalities). By way of example, analyzing ventricle motion is an efficient way to evaluate a degree of ischemia and infarction. In particular, wall motion analysis of the endocardium wall over one heartbeat, or a prescribed portion of the heartbeat, can be performed to quantify the elasticity and contractility of the left ventricle or to otherwise detect and diagnose wall motion abnormalities.

Conventional methods for assessing myocardial function include manual and automated methods for analyzing wall motion using cardiac imaging such as ultrasound (echocardiography). For instance, manual methods for quantifying left ventricular function include manually tracing endocardial and epicardial borders (counters) that are identified within still ultrasound frames at different portions of the cardiac cycle and obtaining various measurements related to wall motion from the traced borders. With some conventional methods, equations are then applied to the results of such measurements, which make certain geometric assumptions and may include empirically derived modifications to a mathematical model. The results are typically viewed in tabular format on a report page and interpretation of such results requires knowledge of normal ranges.

Another conventional manual method for wall motion analysis in echocardiography (e.g., stress echo) includes segmental wall motion analysis, which requires significant training and experience on the part of the echo cardiographer. With such method, the walls of the left ventricle are divided into a plurality of segments (e.g., 16 or 17) according to a prevailing model recommended by the American Society of Echocardiography (ASE). Various standard ultrasound views are obtained to acquire image data information for each LV segment, wherein the standard views are obtained such that the plurality of segments roughly align with a presumed distribution of the three major coronary artery segments. The echo cardiographer will then visually inspect the acquired image data to assess global function and regional abnormalities and then based on his/her assessment, assign a wall motion score to each segment in accordance with a an ASE recommended standard scoring scheme. In particular, the echo cardiographer will visually assess the absolute and relative segmental systolic excursion and timing of excursion to provide some qualitative assessment of each imageable segment. The collective assessments result in a report of negative (non-pathological) or positive (pathological) findings.

A primary concern in the field of echocardiography is the variability in wall motion scoring due to the subjectivity in analyzing wall motion, especially for stress echocardiography, which presents a significant impediment to, e.g., diagnosis of coronary artery disease. Indeed, the accuracy of such echocardiogram reports are directly related to the experience of the operator. Indeed, there is often more "art" involved in such diagnosis than "science." Cardiologists stress the importance of improving wall motion scoring in echocardiography.

Conventional methods for assessing myocardial function include automated methods for analyzing wall motion using cardiac imaging. For example, one conventional method includes automated border detection based on analysis of integrated backscatter, which provides an automated estimate of LV function indices, but does not address segmental or global wall function. Other methods for automatic wall motion analysis generate parametric images indicating excursion, but provide no quantitative comparison amongst segments. One conventional method known as the automated segmental motion analysis (A-SMA) system includes methods for automated border detection to determine the LC cavity and surrounding tissue, and displaying a parametric image of fractional area change. This index was also displayed as a numeric graph for six segments equi-spaced segments in the parasternal short axis view.

While automated methods for wall motion analysis can provide parametric images and generate indices related to wall motion, such methods do not provide automated assessment, or otherwise identify or characterize the condition (e.g., normal or abnormal) of the myocardial tissue.

SUMMARY OF THE INVENTION

Exemplary embodiments of the invention generally include systems and methods for providing automated diagnosis and decision support for cardiac imaging. More specifically, exemplary embodiments of the invention include CAD (computer-aided diagnosis) systems and applications for cardiac imaging, which implement automated methods for extracting and analyzing relevant features/parameters from a collection of patient information (including image data and/or non-image data) of a subject patient to provide automated assistance to a physician for various aspects of physician workflow including, for example, automated assessment of regional myocardial function through wall motion analysis, automated diagnosis of heart diseases and conditions such as cardiomyopathy, coronary artery disease and other heart-related medical conditions, and other automated decision support functions to assist physician workflow.

In other exemplary embodiments of the invention, CAD systems and methods for cardiac imaging implement machine-learning techniques that use a set of training data that is obtained (learned) from a database of labeled patient cases in one or more relevant clinical domains and/or expert interpretations of such data to enable the CAD systems to "learn" to properly and accurately analyze patient data and make proper diagnostic assessments and decisions for assisting physician workflow.

These and other exemplary embodiments, features and advantages of the present invention will be described or become apparent from the following detailed description of exemplary embodiments, which is to be read in connection with the accompanying drawings.

DETAILED DESCRIPTION OF EXEMPLARY EMBODIMENTS

In general, exemplary embodiments of the invention as described below include systems and methods for providing automated diagnosis and decision support for cardiac imaging. More specifically, exemplary embodiments of the invention as described below with reference to FIGS. 1~4, for example, include CAD (computer-aided diagnosis) systems and applications for cardiac imaging, which implement automated methods for extracting and analyzing relevant features/parameters from a collection of patient information (including image data and/or non-image data) of a subject patient to provide automated assistance to a physician for various aspects of physician workflow including, for example, automated assessment of regional myocardial function through wall motion analysis, automated diagnosis of heart diseases and conditions such as cardiomyopathy, coronary artery disease and other heart-related medical conditions, and other automated decision support functions to assist physician workflow. The exemplary CAD systems implement machine-learning techniques that use a set of training data that is obtained (learned) from a database of labeled patient cases in one or more relevant clinical domains and/or expert interpretations of such data to enable the CAD systems to "learn" to properly and accurately analyze patient data and make proper diagnostic assessments and decisions for assisting physician workflow.

Figure 1:
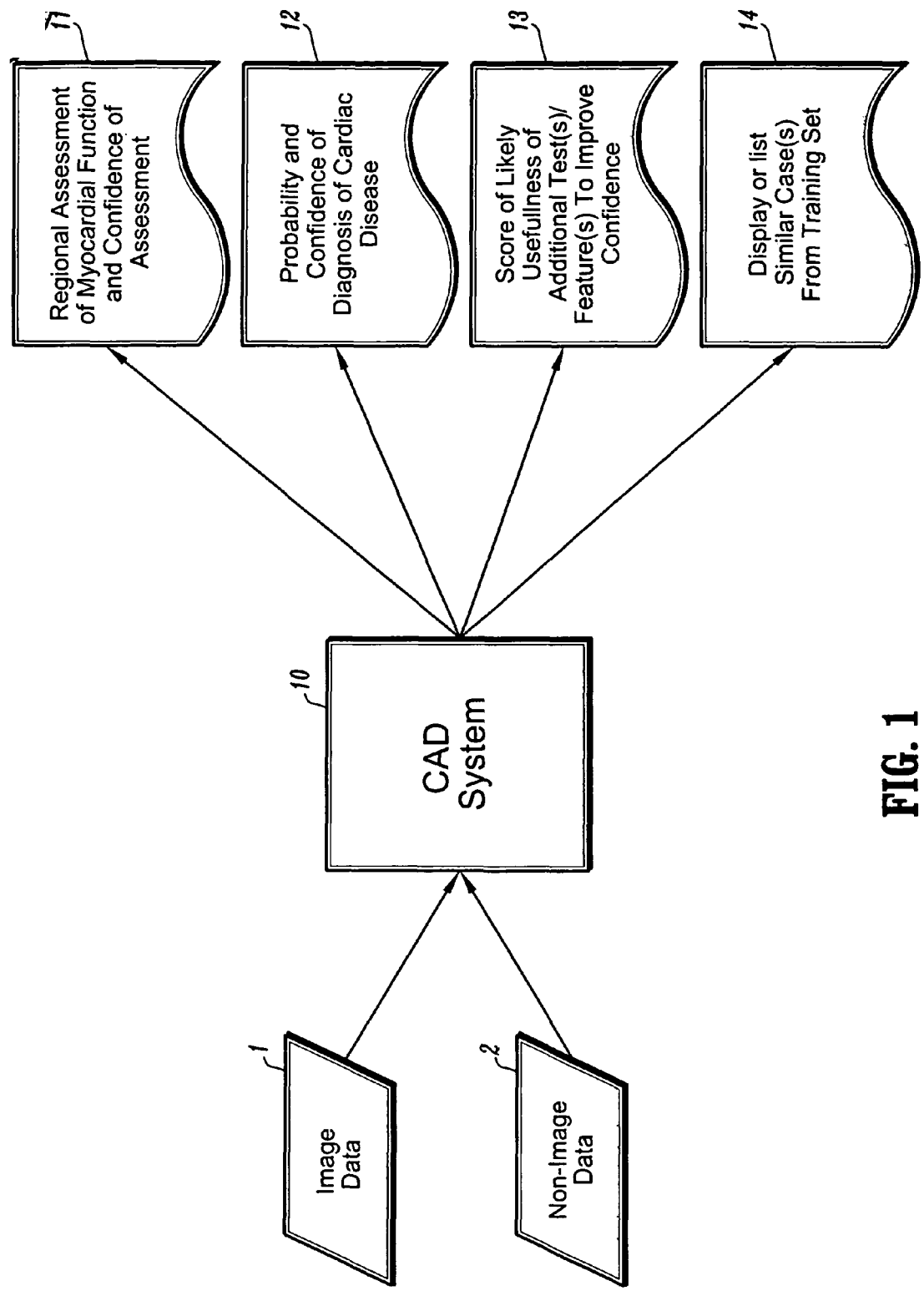
FIG. 1 is a block diagram of a system for providing automatic diagnostic and decision support for cardiac imaging according to an exemplary embodiment of the invention.
Figure 2:
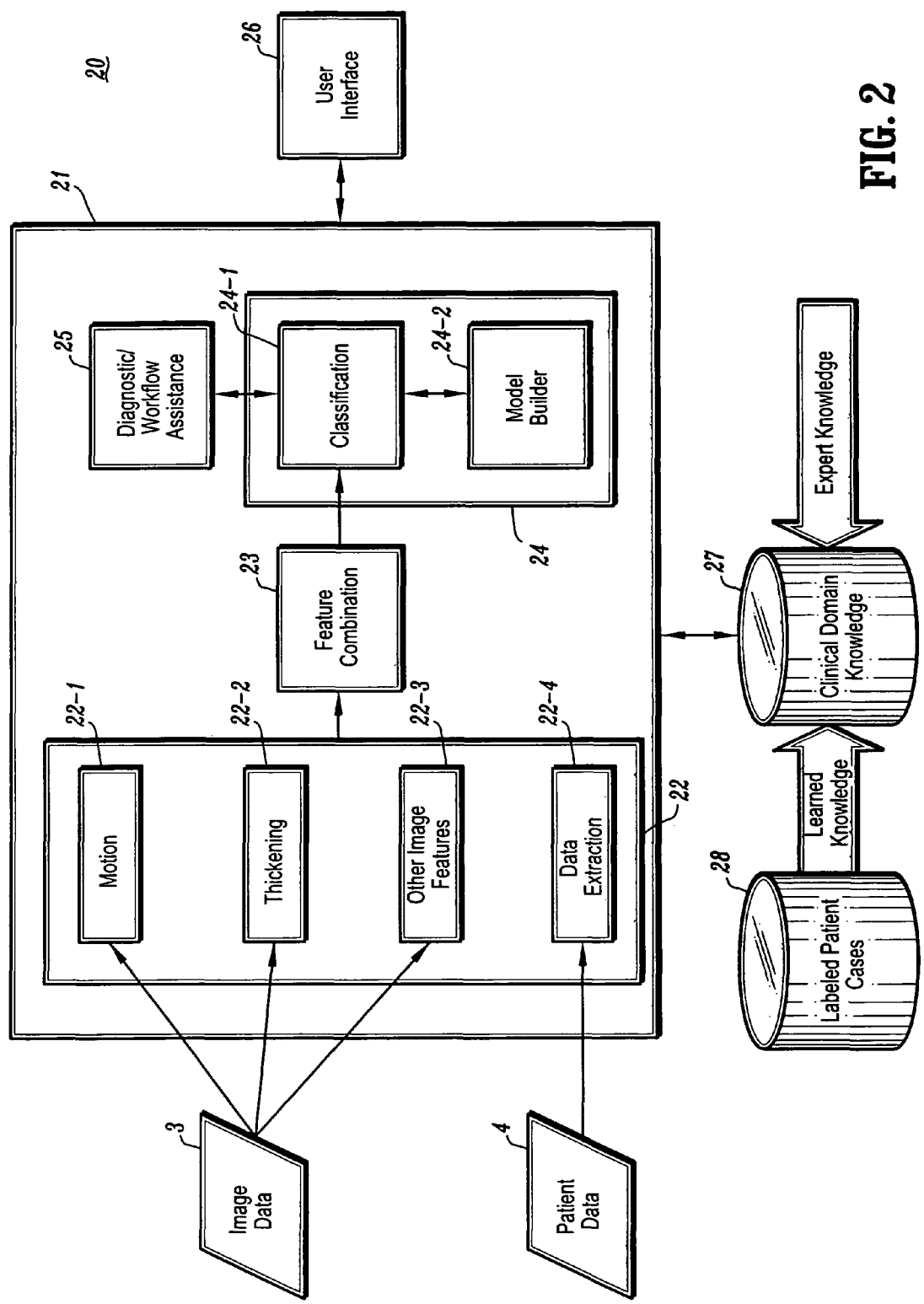
FIG. 2 is a block diagram of a system for providing automatic diagnostic and decision support for cardiac imaging according to another exemplary embodiment of the invention.
Figure 3:
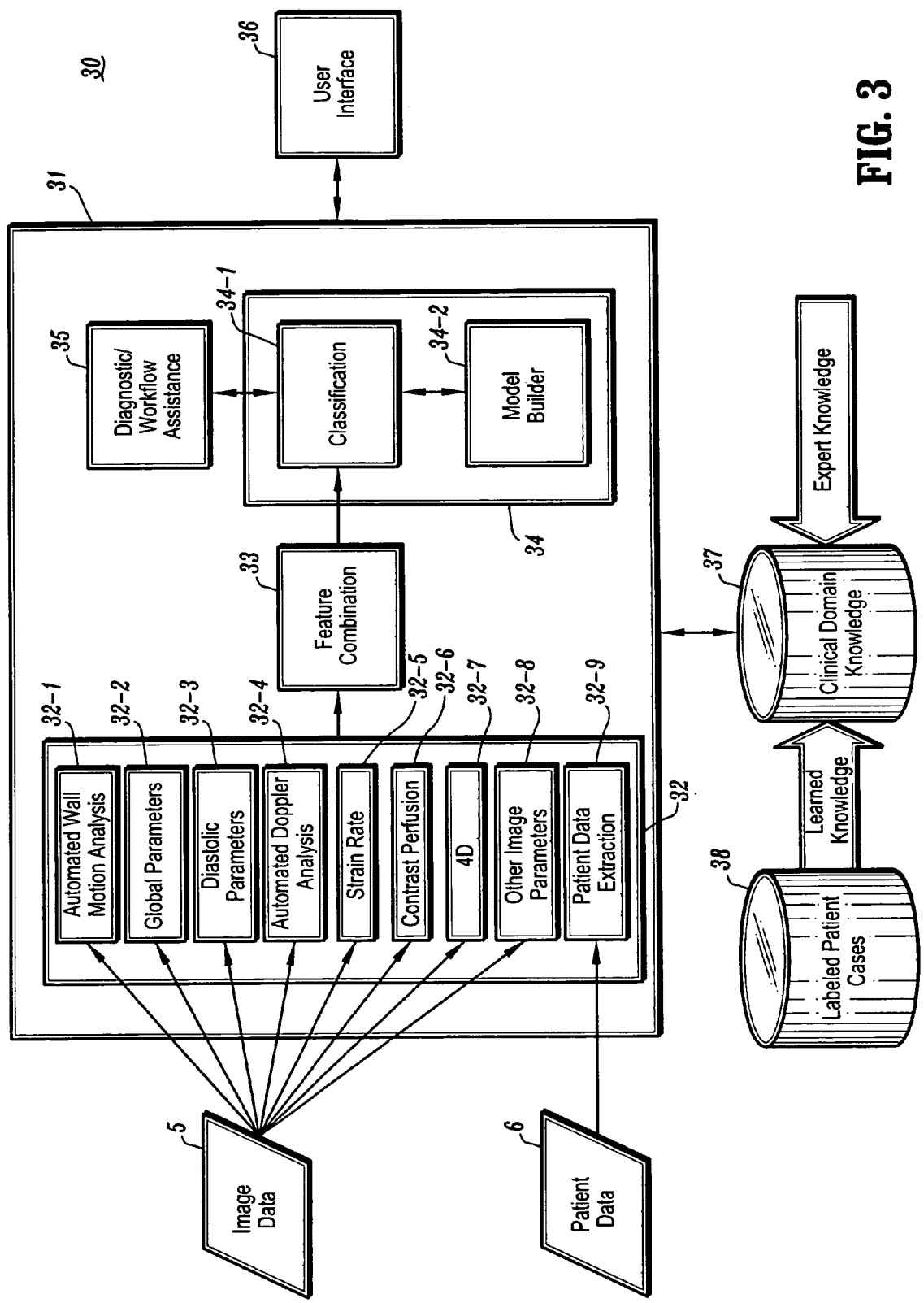
FIG. 3 is a block diagram of a system for providing automatic diagnostic and decision support for cardiac imaging according to another exemplary embodiment of the invention.
Figure 4:
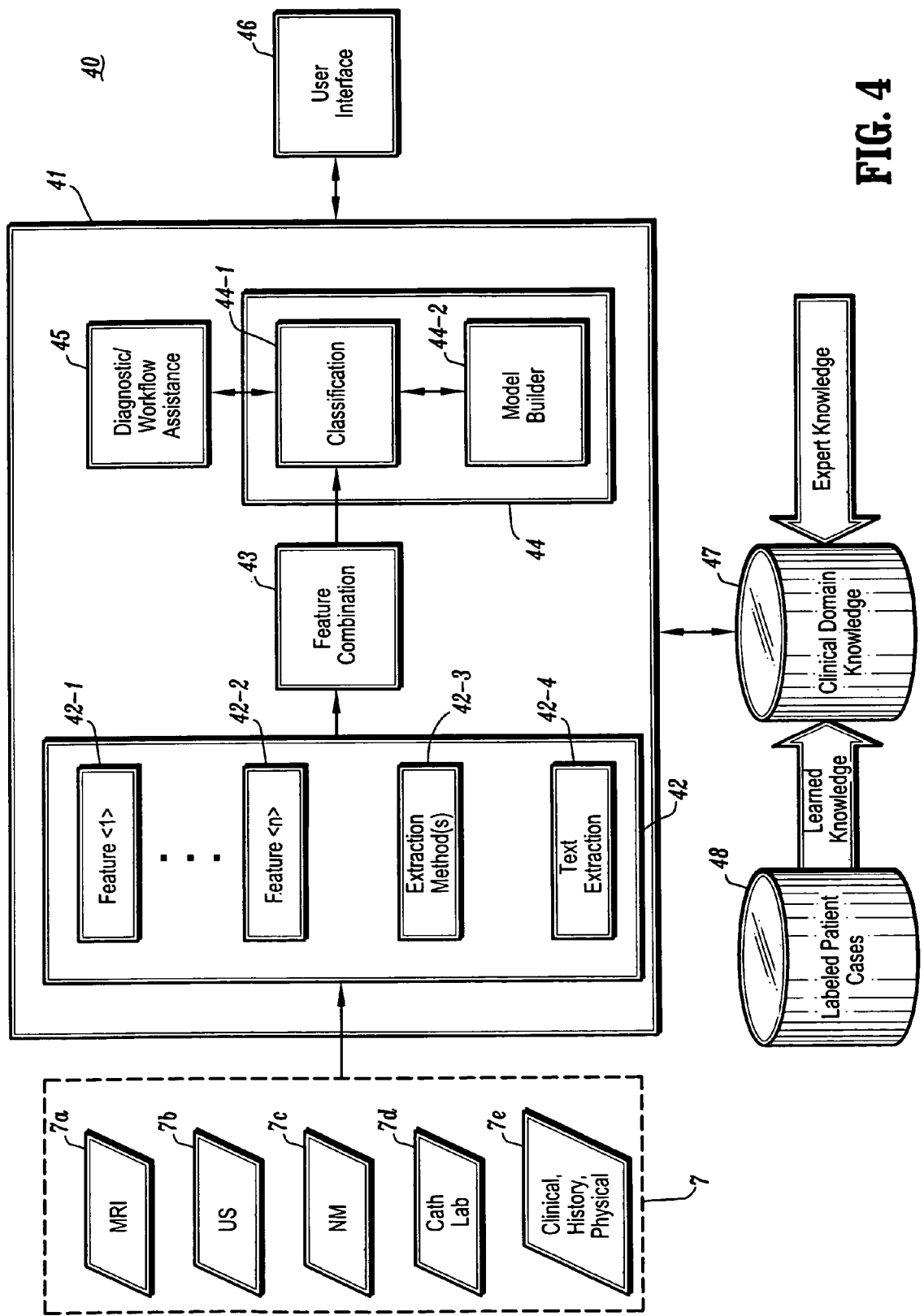
FIG. 4 is a block diagram of a system for providing automatic diagnostic and decision support for cardiac imaging according to another exemplary embodiment of the invention.

In general, FIG. 1 illustrates a general embodiment of a CAD system and method for cardiac imaging which supports one or more imaging modalities and provides one or more decision support functionalities for various aspects of physician workflow. FIGS. 2-4 are specific exemplary embodiments of CAD systems and methods, which are based on the framework of FIG. 1. For example, exemplary embodiments of CAD systems and methods according to the invention will be discussed with referenced to FIG. 2, for example, which can be implemented in ultrasound cardiac imaging applications to provide automated assessment of regional myocardial function, as well as providing decision support functionalities with regard to assessment of regional myocardial function. As explained below, exemplary embodiments of CAD systems that are based on the exemplary framework of FIG. 2 employ classification methods to classify the condition of myocardial tissue in regions of myocardial walls of a heart based on various parameters extracted from cardiac ultrasound image data and, optionally, clinical data records.

Furthermore, exemplary embodiments of CAD systems and methods according to the invention will be discussed with reference to FIG. 3, for example, which can be implemented in ultrasound cardiac imaging applications to provide automated diagnosis for heart disease and conditions such as cardiomyopathy, coronary artery disease and other related conditions, as well as providing decision support functionalities with regard to diagnostic decision regarding cardiac conditions. As explained below, exemplary embodiments of CAD systems that are based on the exemplary framework of FIG. 3 incorporate wall motion analysis and classification methods for assessing regional myocardial function for purposes of providing automated diagnosis and decision support for cardiac diseases and conditions.

Moreover, exemplary embodiments of multi-modal CAD systems and methods according to the invention will be discussed with reference to FIG. 4, for example, which implement methods for providing automated diagnostic and decision support for cardiac imaging for plurality of imaging modalities including cardiac ultrasound image data.

It is to be understood that the systems and methods described herein in accordance with the present invention may be implemented in various forms of hardware, software, firmware, special purpose processors, or a combination thereof. In one exemplary embodiment of the invention, the systems and methods described herein are implemented in software as an application comprising program instructions that are tangibly embodied on one or more program storage devices (e.g., magnetic floppy disk, RAM, CD Rom, DVD, ROM and flash memory), and executable by any device or machine comprising suitable architecture.

It is to be further understood that because the constituent system modules and method steps depicted in the accompanying modal Figures can be implemented in software, the actual connections between the system components (or the flow of the process steps) may differ depending upon the manner in which the application is programmed. Given the teachings herein, one of ordinary skill in the related art will be able to contemplate these and similar implementations or configurations of the present invention.

FIG. 1 is a high-level block diagram illustrating a system for providing automatic diagnostic and decision support for cardiac imaging according to an exemplary embodiment of the invention. More specifically, FIG. 1 illustrates a CAD (computer-aided diagnosis) system (10) that implements methods for analyzing various types of patient information (1) and (2) of a subject patient to provide diagnostic assessments and recommendations and other decision support to assist a physician in various aspects of physician workflow with respect to the subject patient. The CAD system (10) uses machine learning methods that enables the CAD system (10) to continually learn to analyze the patient information (1, 2) and continually provide more accurate diagnostic assessments and/or decisions to assist physician workflow.

The input to the CAD system (10) comprises various sources of patient information including image data (1) in one or more imaging modalities (e.g., ultrasound image data, MRI data, nuclear medicine data, etc.) and non-image data (13) from various structured and/or unstructured data sources, including clinical data which is collected over the course of a patient's treatment and other information such as patient history, family history, demographic information, financial information, and any other relevant patient information. For instance, a specific example of clinical data that may be provided to the CAD system (10) includes clinical variables that have been identified as specific risk factors for and/or predictors of cardiac disease, such as those parameters in the well known "Framingham Study" for cardiac risk analysis: gender, age, diabetic, cardiac history, total cholesterol, HDL, systolic blood pressure, and smoking. The CAD system (10) implements methods for automatically extracting information (features) from the image data (1) and non-image data (2) and combining the extracted information in a manner that is suitable for analysis by the CAD system (10). Depending on the diagnostic and decision support function(s) supported by the CAD system (10), the CAD system (10) can generate one or more outputs (11), (12), (13), and/or (14) which, as explained below, provide physician workflow assistance for screening and diagnosing cardiac diseases and conditions.

For example, in one exemplary embodiment of the invention, the CAD system (10) can extract and analyze information (image parameters/features) from one or more imaging modalities data (1) (e.g., ultrasound image data, MRI data, nuclear medicine data, PET data, CT data, etc.) and (optionally) non-image data (2) to automatically assess regional myocardial function through a wall motion analysis using the extracted information (11). For example, various exemplary embodiments of the invention for providing automated assessment of regional myocardial function will be discussed below with reference to FIG. 2, for example, using one or more classification methods (or other machine leaning methods, including ensemble-based learning methods that learn a multiplicity of classifiers), model-based methods (which try to model various factors related to cardiac function or specific kinds of abnormal motion, for example, by Bayesian inference), or various combinations of such methods, for automatically classifying the condition of myocardial tissue in regions of myocardial walls of a heart using various parameters extracted from cardiac ultrasound image data and, optionally, clinical data records. It is to be understood that the term "classifiers" as used herein generally refers to various types of classifier frameworks, such as hierarchical classifiers, ensemble classifiers, etc. For example, a hierarchical classifier may be designed, for instance, such that a classifier is first used to divide segments into two groups (for example, normal vs. abnormal), and then abnormal segments are further classified as akinetic, diskinetic, etc. In addition, a classifier design can include a multiplicity of classifiers that attempt to partition data into two groups (e.g., diskinetic vs. everything else, akinetic vs. everything else, etc.) and organized either organized hierarchically or run in parallel and then combined to find the best classification. Further, a classifier can include ensemble classifiers wherein a large number of classifiers (referred to as a "forest of classifiers") all attempting to perform the same classification task are learned, but trained with different data/variables/parameters, and then combined to produce a final classification label. Finally, in addition to providing a regional assessment of a myocardial wall, the CAD system (10) can provide a confidence score or indicator of confidence for each regional assessment.

In another exemplary embodiment of the invention, the CAD system (10) can extract and analyze information (image parameters/features) from one or more imaging modalities data (1) (e.g., ultrasound image data, MRI data, nuclear medicine data, etc.) and (optionally) non-image data (2) to automatically generate and output a probability of diagnosis of cardiac disease and (optionally) a measure of confidence of the diagnosis (12). More specifically, by way of example, the CAD system (10) could extract and analyze relevant features from an ultrasound examination of a patient and provide a current estimate and confidence of diagnosis of a cardiomayopathic condition or coronary heart disease, for example.

Alternatively, for patients with known cardiac disease for example, the CAD system (10) could suggest an course of therapy, in which case, the probability and confidence (12) would refer to the likelihood that the therapy would have the desired (presumably beneficial) impact, which could range from curing the patient from cardiac disease, to a purely palliative treatment whose sole aim would be to improve the quality of life of a patient with terminal cardiac disease. More specifically, the CAD system (10) could in addition to suggesting a therapy, automatically provide a probability and/or measure of confidence that the therapy will have a determined outcome and possible provide a probability and/or measure of confidence that the therapy will not have a determined detrimental impact such as side effects. The probability can be specified as a distribution over possible outcomes both beneficial and detrimental, or a set of distributions over possible outcomes both beneficial and detrimental at one or more time points in the future, or a time-varying distribution over possible outcomes at different times in the future, etc.

In another exemplary embodiment of the invention, the CAD system (10) can automatically determine and specify one or more additional tests (or features) that can be performed (or obtained) for the given patient to improve the confidence of a regional assessment of myocardial function or to improve the confidence of a diagnosis of cardiac disease. For example, the CAD system (10) can determine and output a "score" (13) for each additional test or feature, which provides some measure or indication as to the potential usefulness of the particular imaging modality or feature(s) (including clinical data) that would improve the confidence of an assessment or diagnosis determined by the CAD system (10).

In another exemplary embodiment of the invention, the CAD system (10) can identify and output (via display or list) one or more exemplary case studies that are similar to a current case (14). For example, as noted above and explained in further detail below, the CAD system (10) may comprise a database (or library) of previously labeled (diagnosed) cases, and based on features extracted from patient information input to the CAD system (10) for the subject patient, the CAD system (10) can search and display the n-most relevant cases (or those with a similarity measure above some threshold) from the library for diagnostic assistance. In other words, the CAD system (10) can provide a set of similar cases from the training set, or indeed from any database of previously labeled cases, using the automatically extracted features.

It is to be appreciated that the CAD system (10) function of displaying similar cases in the context of physician workflow can provide significant assistance to the physician. For instance, displaying similar cases can provide training for inexperienced users. Indeed, novice users can review other cases to determine or otherwise understand the basis or reasons why the case interpreted in the way that it was. Moreover, display of similar cases can provide a means for experienced users to confirm the diagnostic results of the CAD system (10). Indeed, in addition to probability of diagnosis for a given condition, the CAD system (10) could display similar cases to justify its assessment. Moreover, displaying similar cases enables assessment of prognosis and treatment. More specifically, by studying similar cases to see how other patients responded to different treatment options, a physician can begin to assess the efficacy of these options for the current patient. Lastly, in relatively rare diagnoses where an individual hospital may have only a few (or no) examples of a particular disease, having such a system would allow collection of such exemplar cases for the particular disease from multiple institutions, thus allowing a relatively large sample of cases for that particular disease.

In view of the above, the CAD system (10) can be generally viewed as an automated system that can assist physician workflow by providing an assessment of the current state of a patient (e.g. probability of likelihood of a particular disease) and determining next best health care or diagnostic paths for the subject patient (e.g., identifying additional tests (or features) that can be obtained, which would likely reduce any ambiguity of the assessment). As noted above, it is to be appreciated that the CAD system (10) implements one or more machine-learning and/or model-based methods whereby the information is learned/derived, and the decisions driven, by data that is collected in a training set of the CAD system (10). In particular, as noted above, the CAD system (10) could include a library of exemplary diagnosed cases from which training data is obtained to teach the CAD system (10). In contrast to "expert systems" which are developed and derived from a set of rules dictated by an expert and translated into code, the CAD system (10) learns to provide accurate diagnostic decisions and provide decision support based on training data that is learned from diagnosed cases or learned from expert knowledge.

It is to be appreciated that various machine learning methods may be implemented by the CAD system (10). For example, the systems and methods described in U.S. patent application Ser. No. 10/702,984, filed on Nov. 6, 2003, by Zhou et al, entitled "System and Method for Real-Time Feature Sensitivity Analysis Based on Contextual Information," which is commonly assigned and incorporated herein by reference, can be used in the CAD system (10) for determining which tests or features may be most relevant for reducing ambiguity of a diagnosis. Essentially, the Zhou approach is to create a model of the process, and determine the relative importance of each feature in reducing ambiguity. Such method can be implemented herein whereby each imaging modality, or diagnostic path, could be described as a set of one or more features. Then, the methods described by Zhou would be used to determine which feature(s) would likely provide the greatest improvement in confidence in a diagnosis or assessment. Other machine learning techniques which learn from a large training set of cases can be implemented in the CAD system (10). For example, various machine learning techniques, such as decision trees, SVM, Bayesian networks, or ensemble-based methods which learn a plurality of classifiers and then combine them to arrive at a final diagnosis, for example, may be used.

It is to be appreciated that the CAD system (10) can provide proper decision support even in the absence of various features or information that can be used for rendering such decisions. This may be achieved by building classifiers that can deal with missing data, or by learning different classifiers to deal with different kinds of data, by using other learning methods to infer the missing values, or by using any of a variety of methods known to those of ordinary skill in the art to perform inference/learning in the absence of some (or all) of the patient data/images. Of course, the confidence of the system will improve with more information that can be provided. In an extreme case where there no information at all for a given patient, the CAD system (10) can provide a physician with some guidance as to an initial step to take with respect to the patient. Various methods for learning and/or performing inference with missing/noisy data may be used in the decision support system.

It is to be appreciated that the above methods can be extended to provide automatic screening for cardiac conditions such as coronary heart disease. For instance, the CAD system (10) can be configured to make a determination, in view of a patient's clinical and family history, as to the likelihood that the patient has (or can develop) coronary artery disease and what screening test (if any) should be given to the patient to best detect potential cardiac conditions. Such determinations can be made using a training set as described above and machine-learning techniques. Moreover, for screening, the CAD system (10) can generate and output decisions as discussed above, including likelihood of disease, exemplar cases from a training set, and the screening test that would be optimal for the given patient.

Referring now to FIG. 2, a block diagram illustrates a system for providing automatic diagnostic and decision support for cardiac imaging according to another exemplary embodiment of the invention. More specifically, FIG. 2 illustrates a CAD system (20) for ultrasound cardiac imaging, which includes methods for automated regional assessment of myocardial function of a heart using various parameters obtained from one or more imaging modalities (e.g., ultrasound image data, MRI data, nuclear medicine data, etc.), as well as non-image data, to analyze myocardial wall motion, according to an exemplary embodiment of the invention. The CAD system (20) of FIG. 2 illustrates one or more exemplary frameworks for the CAD system (10) of FIG. 1 to support one or more ultrasound imaging methods. In general, the CAD system (20) comprises a data processing system (21) which comprises a feature extraction module (22), a feature combination module (23), a classification module (24) and a diagnostic/workflow assistance module (25). The feature extraction module (22) implements various methods (22-1, 22-2, 22-3, 22-4) for extracting relevant parameters from ultrasound image data (3) (and possibly other imaging data) and other sources of non-image patient data (4) such as clinical, family, history data, etc. The patient data may be available in structured form (in a database as a specified value of a particular field) or may be extracted from the patient record (by natural language processing of text, for example). The feature combination module (22) combines the extracted features in a manner that is suitable for input to the classification module (24) for analysis.

The classification module (24) comprises a classification method (24-1) (or classification engine) that analyzes the combined extracted parameters using one or more classification models, which are trained/dynamically adapted via model builder (24-2), to generate information that is used to provide diagnostic and decision support. The diagnostic/workflow assistance module (25) includes one or more methods for implementing functions such as described above with reference to FIG. 1 (e.g., providing a regional assessment of myocardial function, providing a set of cases similar to a current case, providing a score showing the likely benefit of additional features that would improving a confidence of a regional assessment, etc.).

The CAD system (20) further comprises a user interface (26) (e.g., graphical user interface displayed on computer monitor with keyboard and mouse input devices) which enables a user to select one or more functions supported by the diagnostic/workflow assistance module (25) and which enables the system to render and present processing results to the user. The processing results can be rendered and presented to a user in one or more of various ways according to exemplary embodiments of the invention as described below.

The CAD system (20) further comprises a repository (27) that maintains a clinical domain knowledge base of information that is derived from various sources. For instance, the clinical domain knowledge (27) may include knowledge that is learned or automatically extracted from a large database of analyzed/labeled cases (28) related to the clinical domain(s) supported by the CAD system (20). The clinical domain knowledge (27) may include expert clinical knowledge that is input directly by an expert from analyzing previous claims, or information related to rules/regulations/guidelines associated with medical bodies or insurance companies, with regard to the supported clinical domain(s). As explained in detail below, the clinical domain knowledge in repository (27) can be used by the various methods (22, 23, 24, and 25) of the data processing system (21).

In one exemplary embodiment of the invention, the CAD system (20) includes methods for automatically analyzing myocardial wall motion and wall thickness in ultrasound images (3) of a heart of a subject patient, to thereby extract wall motion and wall thickening parameters that are used to automatically classify regional segments of myocardial heart tissue as normal or abnormal. In particular, in one exemplary embodiment of the CAD system (20) as depicted in FIG. 2, the feature extraction module (22) comprises a wall motion extraction module (22-1) for extracting wall motion parameters from ultrasound image data (3), and a wall thickening extraction module (22-2) for extracting wall thickening parameters from the ultrasound image data (3).

In one exemplary embodiment of the invention, the feature extraction modules (22-1, 22-2) implement the methods described in U.S. patent application Ser. No. 10/794,476, filed on Mar. 5, 2003, entitled "System and Method for Tracking a Global Shape of an Object in Motion,", which is commonly assigned and fully incorporated herein by reference. Briefly, this application describes methods for, e.g., tracking the global shape and/or local motion of a myocardial wall of a heart (e.g., an endocardial wall and/or epicardial wall of the heart) in echocardiogram images (2 dimensional, 3 dimensional and 4 dimensional (3D+time)) for medical analyses of a heart that evolves over time. These methods can be used in an echocardiograph system for tracking the endocardial wall of the left ventricle from 2D, 3D, or 4D (3D+time) images of the heart from various perspectives. These methods can be used for tracking the magnitude, direction and timing of a motion for various portions of a myocardial wall. Moreover, these method can be used for tracking the inner and outer contours of a myocardial wall over a time frame (e.g., systole phase) to provide wall thickening data over such time frame.

In contrast to conventional methods used in echocardiography, for example, which only consider wall motion information, the thickening of the heart wall during the systole phase is important to consider. Indeed, even when one portion of the heart wall is dead, such portion may be pulled along by nearby segments of the wall—a phenomenon known and referred to as "tethering", which could lead to an improper analysis. Advantageously, consideration of both wall motion and wall thickening provides a more accurate assessment of the health of the underlying wall.

Accordingly, in one exemplary embodiment of the invention as noted above, the data processing system (21) extracts wall motion and wall thickening parameters for regional sections of a desired myocardial heart wall to assess the condition of the heart wall on a regional basis. In one exemplary embodiment of the invention, the assessment or classification results output from the classification module (24) include a wall motion "score" for one or more regions of the heart wall. The diagnostic/workflow assistance module (25) will render the classification results for display to the via the user interface (26). In particular, in one exemplary embodiment of the invention, the classification results will be presented to the user as a wall motion "score" for various segments of the left ventricle of the heart in accordance with a recommended standard of the American Society of Echocardiography (ASE). In particular, under the ASE standard, the Left Ventricle is divided into a plurality of segments (e.g., 16 or 17). The ASE recommends using standard ultrasound views (A4C, A2C, PSAX, PLAX, ALAX views in B-mode) to obtain image data for the various segments and analyzing such image data to assign each segment a wall motion score as follows: 1=normal; 2=hypokinesis; 3=akinesis; 4=dyskinesis; and 5=aneurysmal. (See e.g., Schiller et al, "Recommendations for Quantization of the Left Ventricle by Two-Dimensional Ultrasound", Journal of American Society of Echocardiography, vol 2, p. 358, 2889, and Snyder et al)

Figure 5:
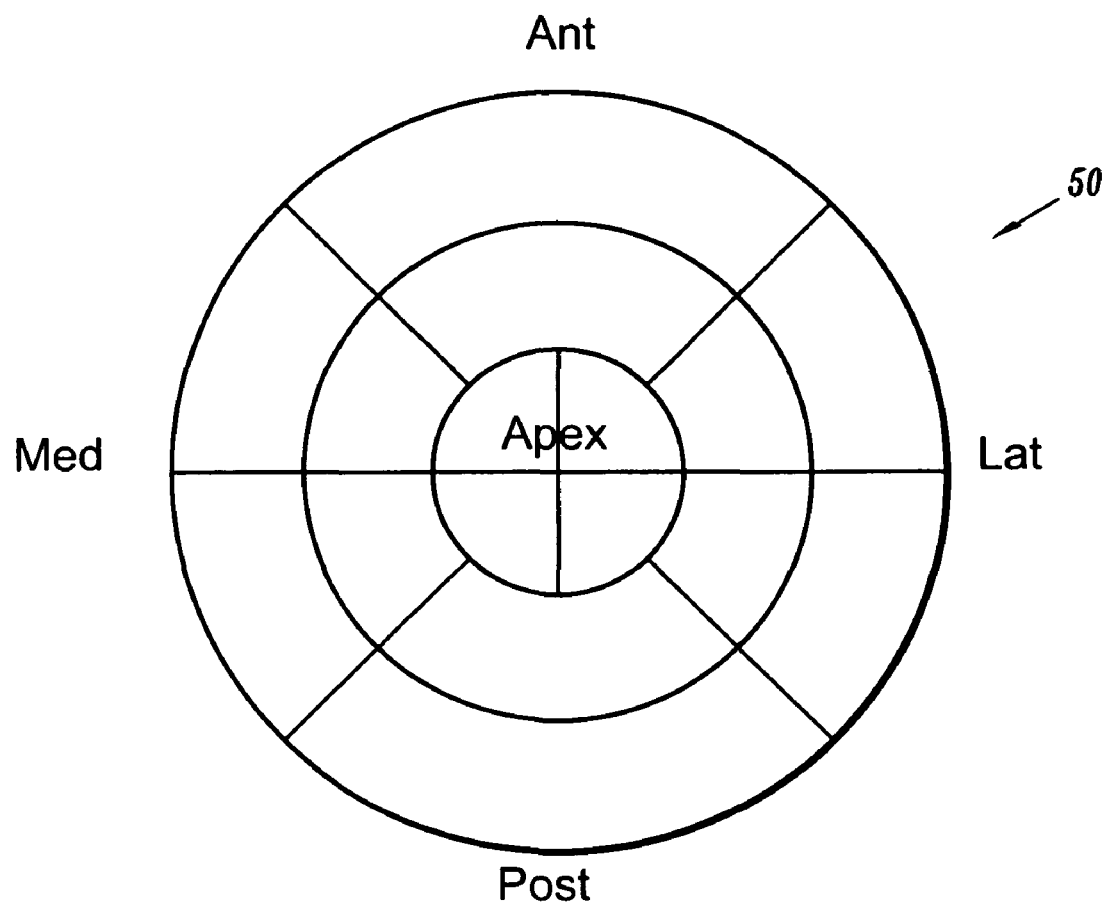
FIG. 5 is an exemplary two-dimensional representation of a plurality of segments of a heart ventricle, which can used to display wall motion scores in a graphical user interface, according to an exemplary embodiment of the invention.

In an exemplary embodiment wherein a scoring technique recommended by the ASE is used, the classification results (which include the ASE scores) can be displayed in a "bullseye" plot, as shown in FIG. 5. More specifically, FIG. 5 illustrates 2D plot (50) based on a 16-segment model of the LV of the heart, wherein 16 segments are shown in a 2D representation of the 3D LV cavity, along with standard orientation data denoted as Ant, Med, Lat, Post, Apex. In accordance with one exemplary embodiment of the invention, the processing results of the classification module (24) of FIG. 2 are presented as a wall motion "score" on the scale from 1-5 based on the ASE recommendation for each segment, which scores are presented to the user in the 2D plot. The scores can be displayed by including the actual scores in the segments or by coloring the segments according to the scores. Other methods for presenting the scores are readily envisioned by one of ordinary skill in the art.

It is to be appreciated that in other exemplary embodiments of the invention, rather than ASE-defined segments, classification of normal and abnormal tissue can be performed at every point in an image or in specified sub-regions.

It is to be understood that a wall motion analysis process according to the invention can be implemented using other imaging modalities. For example, a method for segmenting the left ventricle in cardiac MR images can be employed, such as described in the article by Jolly, et. al., entitled *Segmentation of the Left Ventricle in Cardiac MR Images; Proc. of the International Conference on Computer Vision, ICCV* 2001; Vancouver, Canada; July 2001, Vol 1, pp 501-508). Such a technique could be used to extract motion and thickening data from MR images in an analogous way to the techniques described above for ultrasound. Analogous techniques can be used for CT images as well.

In other exemplary embodiments of the invention, in addition to providing a regional assessment of the heart wall, the classification module (24) can include methods for determining a confidence level for each segment, which represents the confidence in the assessment (e.g., wall motion score) for the given segment. Indeed, due to differences in image quality as well as variations in body habitus and other factors, different assessments may have different levels of confidence, even within the same person. For example, if regional wall motion is only considered, it is often the case for an echo cardiographer that the confidence of the analysis of the septum, where the signal strength is strong, is usually better than their confidence of analysis of the lateral wall, where signal strength is poor. The echo cardiographer automatically considers such information when assessing a patient. However, conventional automated systems just show a result without a corresponding confidence analysis. In accordance with one exemplary embodiment of the invention, in the case of regional wall motion analysis, each segment can be assigned a score from 1-5, as per ASE guidelines, along with a confidence indicator for each segment (perhaps on a scale of 1-10).

It is to be appreciated that in other exemplary embodiments of the CAD system (20) of FIG. 2, one or more additional features can be extracted and considered for providing automated regional assessment of myocardial function. More specifically, in other exemplary embodiments of the invention, the feature extraction module (22) can implement other parameter extraction methods (22-3) for extracting other relevant image parameters for analysis by the classification process (24-1) to automatically analyze wall motion and characterize/classify normal and abnormal segments of myocardial walls, in accordance with the present invention. For example, in addition to wall motion and wall thickening data, automated diagnosis and assessment can be based on parameters such as fractional wall shortening, fractional area change, maximum excursion, phase of maximum excursion (i.e. what point of the heart cycle does maximum excursion occur), velocity (absolute or relative) of excursion, and strain or strain rate of the myocardial tissue, wherein such parameters can extracted from one or more of various types of ultrasound image data (3) over an entire heart cycle, or a prescribed portion of the heart cycle, such as systole.

More specifically, in accordance with other exemplary embodiments of the invention, one or more additional regional measurements can be extracted from ultrasound image data (3) and combined into the analysis into an overall regional assessment of the heart wall. For example, the feature extraction module (22) may implement one or more additional feature extraction methods (23-3) for extracting regional parameters such as tissue velocity and strain and strain rate. As is known in the art, tissue velocity, strain, and strain rate imaging can be used to provide regional assessment of myocardial tissue. These assessments are typically given in isolation as an image for the echo cardiographer to assess. Often, these velocity and strain rate images have artifacts that may be difficult to assess, and may lead to error of interpretation. However, by extracting features from these, and combining them with other features, a more accurate assessment of regional assessment can be made.

Another regional parameter that extracted from ultrasound images (3) includes contrast perfusion. Perfusion is the measurement of blood into the heart wall and contrast imaging methods can be used to acquire ultrasound image data from which contrast perfusion parameters can be extracted for assessing regional myocardial function. Again, by combining perfusion features with other features, a better assessment of regional function can be obtained Another parameter that can be considered for assessing regional myocardial function includes timing data such as timing of the start of contraction. Indeed, it is known that myocardial walls (or portions thereof) that are dead or injured may begin to contract later than other myocardial walls (or other portions thereof). Accordingly, timing parameters can be used as addition information for assessing myocardium function. Phase imaging methods can be used to acquire ultrasound image data (3) from timing parameters can be extracted for assessing regional myocardial function.

Furthermore, comparing different segments with one another can provide additional information that is efficacious for assessing myocardial function. Indeed, conventional techniques look at each segment in isolation. However, a significant benefit can be achieved by comparing the different segments of the myocardium with one another. For example, when assessing regional wall motion, the motion of one part of the heart may be deemed slow. However, if that part of the wall is moving at the same speed as other parts of the heart, a different assessment can be made as compared if that part of the wall is moving significantly slower than other parts of the heart.

In another exemplary embodiment of the invention, extraction of parameters from 3D ultrasound data can provide additional advantages over 2D data. Current techniques for wall motion analysis use 2D (+time) data. However, extracting features from 3D (+ time) would be beneficial for a number of reasons. First, a truer picture of velocity would be available, since velocities could be tracked rather than just "in-plane" velocities. Secondly, 2D images suffer because an assumption is made that the same 2D slice is available at all times. Due to motion of the heart, this is not true. Therefore, the combination of motion, thickening, velocity, strain, strain rate, and/or contrast perfusion in 3D for regional myocardial analysis enables a more accurate assessment.

Other parameters that may be implemented for assessing myocardial function include global indices. Conventional automated techniques have relied solely on regional indices, such as motion or strain, to assess regional myocardial function. However, a technique which automatically assesses regional function should also take into account global indices of heart function. These could include, but are not restricted, to the following: left ventricular volume and ejection fraction, left ventricular wall thickness and mass, and diastolic function indicators, such as the E/A ratio While these indicators do not specifically point to a problem in a specific region of the heart, such parameters are generally indicative of coronary artery disease, and provide an additional features for assessment of regional myocardial function.

In other exemplary embodiments of the invention, the data processing system (21) xtracts and analyzes relevant parameters from non-image patient data (4) of a subject patient, which are used in conjunction with the extracted image parameters to provide automated regional assessment of myocardial function. The patient data (4) can include patient information from a plurality of structured and unstructured data sources, which is collected over the course of a patient's treatment. In general, the structured data sources include, for example, financial (billing), laboratory, and pharmacy databases, wherein patient information in typically maintained in database tables. The unstructured data sources include for example, waveform data, free-text based documents of laboratory test results, doctor progress notes, details about medical procedures, prescription drug information, radiological reports, and other specialist reports.

In accordance with an exemplary embodiment of the invention, the non-image patient data (4) can include a significant amount of useful data indicative of coronary heart disease and other related conditions, for example, which can be used for providing automated regional assessment of myocardial function. By way of example, clinical information may be found in history and physical notes, wherein a physician notes that a person has experienced chest pain. In addition, certain diseases, such as diabetes, can increase the potential of a person developing/having coronary artery disease. Other indications, such as cholesterol level, history of smoking, family history of coronary artery disease, age, gender, intima-medial thickness (from ultrasound measurements, for example) etc., can also be used to assess the risk of coronary artery disease.

Accordingly, in the exemplary embodiment of FIG. 2, the feature extraction module (22) includes one or more patient data extraction methods (22-4) for extracting relevant patient data from structured and/or unstructured patient data records (4), which are relevant for the medical condition under assessment. With respect to the exemplary embodiment of regional myocardial assessment, the clinical data may not pinpoint specific regions where myocardial function is poor, but such clinical data can be helpful overall in assessment of regional myocardial function. It is to be appreciated than any suitable data analysis/data mining methods may be implemented by the extraction module(s) (22-4) for extracting relevant parameters from the patient data records (4), and to deal with errors/inconsistencies/missing information in the patient record. In one exemplary embodiment of the invention, patient data extraction methods (22-4) and feature combination method (23) may be implemented using the data mining methods and feature combination methods as described in commonly assigned and copending U.S. patent application U.S. Ser. No. 10/287,055, filed on Nov. 4, 2002, entitled "Patient Data Mining", which claims priority to U.S. Provisional Application Ser. No. 60/335,542, filed on Nov. 2, 2001, which are both fully incorporated herein by reference.

Briefly, U.S. Ser. No. 10/287,055 describes data mining methods for extracting relevant information from clinical data records using domain-specific knowledge contained in a knowledge base (e.g., in repository (27)), which are represented as probabilistic assertions about the patient at a particular time (referred to as elements) and combining all elements that refer to the same variable (domain-specific criteria) at a given time period to form a single unified probabilistic assertion regarding that variable, and then to reconcile that information over time to deal with changes in the value of that variable (including applying temporal constraints about how the variable can change over time).

Moreover, the methods for combining patient information for assessing risk of coronary heart disease described in U.S. patent application Ser. No. 10/287,085, filed on Nov. 4, 2002, entitled "Patient Data Mining for Cardiology Screening," which is commonly assigned and fully incorporated herein by reference.

In the exemplary embodiment of FIG. 2, as noted above, the data processing system (21) uses clinical domain knowledge data maintained in the repository (27) to perform the various methods such as feature extraction (22), feature combination (23) and model building (24-2b). The domain-specific knowledge base (27) may include disease-specific domain knowledge. For example, the disease-specific domain knowledge may include various factors that influence risk of a disease, disease progression information, complications information, outcomes and variables related to a disease, measurements related to a disease, and policies and guidelines established by medical bodies such as the ACC, AHA and ESC.

By way of example, domain-specific criteria for diagnosing acute myocardial infarction (AMI) may specify diagnosis of AMI depending on the unequivocal presence or absence of a combination of three factors: (i) symptoms of cardiac pain; (ii) changes in EKG (electrocardiogram); and (iii) change in enzymes that are released by injured heart muscle. Moreover, assuming an individual had cardiac pain, the degrees to which changes in EKG and enzymes meet specified criteria, individually and in combination, ca be used to determine the certainty of the diagnosis ("definite", "probable", or "possible"), or presented as a numeric certainty (for example, between 0% and 100%).

The domain-specific knowledge base (27) may also include institution-specific domain knowledge. For example, this may include information about the data available at a particular hospital, document structures at a hospital, policies of a hospital, guidelines of a hospital, and any variations of a hospital.

The clinical domain knowledge base (27) may be derived from various sources. For instance, the clinical domain knowledge base (27) may include knowledge that is learned from a large database of analyzed/labeled cases (28). In addition, the clinical domain knowledge base (27) may include knowledge that is input by an expert from analyzing previous claims, or from rules and regulations published by an insurance company, for example. The data in the domain knowledge base (27) can be encoded as an input or as programs that produce information that can be understood by the system. As noted above, the domain expert data may be obtained by manual input from a domain expert using an appropriate user interface or the domain expert data may be automatically or programmatically input.

The extraction modules (22-4) can use relevant data in the domain knowledge base (27) to extract relevant parameters and produce probabilistic assertions (elements) about the patient that are relevant to an instant in time or time period. The domain knowledge required for extraction is generally specific to each source. For example, extraction from a text source may be carried out by phrase spotting, wherein a list of rules are provided that specify the phrases of interest and the inferences that can be drawn therefrom. For example, if there is a statement in a doctor's note with the words—"There is evidence of cardiomyopathy in left ventricle of the heart"— then, in order to infer from this sentence that the patient has cardiomyopathy, a rule can be specified that directs the system to look for the phrase "cardiomyopathy," and, if it is found, to assert that the patient has cardiomyopathy with a some degree of confidence. Extraction from a database source may be carried out by querying a table in the source, in which case, the domain knowledge needs to encode what information is present in which fields in the database. On the other hand, the extraction process may involve computing a complicated function of the information contained in the database, in which case, the domain knowledge may be provided in the form of a program that performs this computation whose output may be fed to the rest of the system.

The methods implemented by the feature combination module (23) can be those described in the above-incorporated patent applications. For example, a feature combination method can be a process of producing a unified view of each variable at a given point in time from potentially conflicting assertions from the same/different sources. In various embodiments of the present invention, this is performed using domain knowledge regarding the statistics of the variables represented by the elements.

The model builder (24-2) builds classification models implemented by the classification method (24-1), which are trained (and possibly dynamically optimized) to analyze various extracted features provide diagnostic assistance and assessment on various levels, depending on the implementation. It is to be appreciated that the classification models may be "black boxes" that are unable to explain their prediction to a user (which is the case if classifiers are built using neural networks, example). The classification models may be "white boxes" that are in a human readable form (which is the case if classifiers are built using decision trees, for example). In other embodiments, the classification models may be "gray boxes" that can partially explain how solutions are derived (e.g., a combination of "white box" and "black box" type classifiers). The type of classification models that are implemented will depend on the domain knowledge data and model building process (24-2). The type of model building process will vary depending on the classification scheme implemented, which may include decision trees, support vector machines, Bayesian networks, probabilistic reasoning, etc., and other classification methods that are known to those of ordinary skill in the art.

The model builder/update process (24-2) uses data in the clinical domain knowledge base (27) to train classification models, and possibly dynamically update previously trained classification models that are implemented by the classification process (24-1). In one exemplary embodiment of the invention, the model builder/update process (24-2) is implemented "off-line" for building/training a classification model that learns to assess regional myocardial function. In another exemplary embodiment of the invention, the model builder/update process (24-2) employs "continuous" learning methods that can use the domain knowledge data in repository (27) which is updated with additional learned data derived from newly analyzed patient data or otherwise optimize the classification model(s) associated with the relevant condition. Advantageously, a continuous learning functionality adds to the robustness of the CAD system (20) by enabling classification methods (24-1) to continually improve over time without costly human intervention.

In the exemplary CAD system (20) of FIG. 2, as noted above, the diagnostic/workflow assistance module (26) can provide one or more diagnostic and decision support functions as described above with reference to FIG. 1. For instance, the diagnostic/workflow assistance module (26) can command the classification module (24) to provide an assessment of regional myocardial function together with a measure of confidence in the assessment, based on a set of features extracted from ultrasound image data (3) and/or non-image patient data records (4). The classification engine (25-1) could perform such classification using one or more classification models that are trained to analyze the combined features output from module (23). In another exemplary embodiment, the diagnostic/workflow assistance module (25) can command the classification module (24) to determine what additional imaging modalities or features (e.g., from B-mode ultrasound image data, other image mode, and/or non-image data) can be obtained and further analyzed to increase the confidence in the regional assessment. Moreover, the diagnostic/workflow assistance module (25) can command the classification module (23) to obtain and display (via user interface) one or more similar patient cases in repository (27) based on the current set of extracted features.

Referring now to FIG. 3, a block diagram illustrates a system for providing automated diagnostic and decision support for cardiac imaging according to another exemplary embodiment of the invention. More specifically, FIG. 3 illustrates a CAD system (30) for providing automated diagnosis of, e.g., coronary heart disease using image parameters obtained from one or more of various ultrasound image modes (B-mode, contrast imaging, and/or phase imaging, etc.) and/or non-image patient data, as well as providing other decision support functions to assist physician workflow. In one exemplary embodiment, the CAD system (30) of FIG. 3 incorporates an automated wall motion classification analysis as discussed above for FIG. 2. The CAD system (30) of FIG. 3 illustrates one or more exemplary frameworks for the CAD system (10) of FIG. 1 to support one or more ultrasound imaging methods.

Referring to FIG. 3, the CAD system (30) comprises a data processing system (31) which implements methods for automatic classification (diagnosis) of heart disease based on various parameters are extracted from ultrasound image data, as well as other methods to assist a physician to decide an a care or diagnosis path for a particular patient. In general, the data processing system (31) comprises a feature extraction module (32), a feature combination module (33), a classification module (34) and a diagnostic/workflow assistance module (35). Moreover, the CAD system (30) comprises a user interface (36) which enables user interaction with the CAD system (30) to select one or more functions supported by the diagnostic/workflow assistance module (35) (e.g., providing automated diagnosis and confidence of diagnosis for one or more types of cardiac conditions, determine what additional ultrasound imaging modalities or features (e.g., from B-mode ultrasound image data, other image mode, and/ or non-image data) can be obtained and further analyzed to increase the confidence in diagnosis, obtain and display one or more similar patient cases in a repository (38) based on the current set of extracted features.)

The feature extraction module (32) implements various methods (32-1~32-9) for extracting relevant parameters from one or more of various modes of ultrasound image data (5) and non-image patient data (6), which can be analyzed to provided automated diagnosis of heart disease and other types of decision support as discussed below. For instance, the feature extraction module (32) includes an automated wall motion analysis module (32-1) which implements the methods discusses above with reference to FIG. 2, for providing a regional assessment of myocardial function based on motion and thickening parameters extracted from ultrasound images. The parameters that are output from the module (32-1) can be the actual results of the assessment (e.g., wall motion scores for each segment) or the extracted motion and thickening parameters, which are further processed by the classification module (34) to provide automated diagnosis of heart condition or provide other diagnostic support functions.

Other extraction modules include a global parameter extraction module (32-2) for extracting global parameters from ultrasound image data, including for example, LVEF (left ventricular ejection fraction), LVEDV (left ventricular end diastole volume), LVESV (left ventricular end systole volume), etc. and a diastolic parameter extraction module (32-3) for extracting diastolic parameters such as E/A ratio, etc, which provide general indications of coronary heart disease. Moreover, blood velocities may be extracted from Doppler images in ultrasound (32-4). Moreover, regional parameters can be extracted from ultrasound images including a strain rate parameter extraction module (32-5) for extracting strain and strain rate data, a contrast perfusion module (32-6) for extracting perfusion features from contrast imaging, a 4D extraction module (32-7) for extracting features from 3D (+time) ultrasound images and other image feature extraction methods (32-8) for extracting relevant parameters from ultrasound image data for the same or additional modes. The various feature extraction methods (32-1~32-9) implemented by the feature extraction module (32) are the same or similar to those methods discussed above with reference to FIG. 2. Various methods that may be implemented for extracting features from ultrasound images and other image data as noted above are well known to those of ordinary skill in the art, and any suitable known extraction method or methods may be implemented for the extraction module (see, e.g., "Myocardial Perfusion Assessment With Contrast Echocardiography", Medical Imaging 2001: Ultrasonic Imaging and Signal Processing, Michael F. Insana, K. Kirk Shung, Editors, Proceedings of SPIE Vol. 4325 (methods for contrast perfusion for ultrasound); Hashimoto et al, "Myocardial strain rate is a superior method for evaluation of left ventricular subendocardial function compared with tissue Doppler imaging", J Am Coll. Cardiol. 2003 November 5; 42(9):1584-6. (methods for strain and strain rate imaging in ultrasound); and G. I. Sanchez-Ortiz, et al., "Automated LV motion analysis from 3D echocardiography", *Medical Image Understanding and Analysis* (*MIUA*) *Conference* 1999, Oxford UK, pp. 85-88 (methods for extraction of parameters from 3D ultrasound images), etc.). In the exemplary embodiment of FIG. 2, such features are used for, e.g., automated assessment of regional myocardial function, whereas in the system of FIG. 3, such features are further used, e.g., for automated diagnosis of heart-related diseases.

The feature combination module (33) combines a set of extracted features in a manner that is suitable for input and analysis by the classification module (34). The classification module (34) comprises classification methods (34-1) to analyze the combined extracted parameters using one or more classification models, which are trained/dynamically adapted via model builder (34-2), to provide automatic diagnosis of heart disease and other decisions support functions. The CAD system (30) further comprises a repository (37) that maintains a clinical domain knowledge base of information which provides training data used by the model builder (34-2) to build/train classification models used by the classification methods (34-1). A large database of analyzed/labeled cases (38) related to the clinical domain or domains supported by the CAD system (30) can be used to obtain training data in repository (37). The clinical domain knowledge (37) may include expert clinical knowledge that is input directly by an expert from analyzing previous claims, or information related to rules, regulations and/or guidelines associated with medical bodies or insurance companies with respect to the supported clinical domain(s). The clinical domain knowledge in repository (37) can be used by the various methods (32, 33, 34 and 35) of the data processing system (31).

It is to be appreciated that the various modules (32, 33, 34 and 35) in FIG. 3 can implement the same or similar methods as those corresponding modules (22, 23, 24 and 25) of the CAD system (20) of FIG. 2 as described above. However, the various methods, such as the classification and model building methods in classification modules (24) and (34), will vary depending on the types of decision support functions, feature extraction methods and/or image modalities supported by the respective CAD systems (20) and (30). Moreover, the clinical domain knowledge base (37) is similar to the knowledge base (27) of FIG. 2, except that the training data in knowledge bases (27) and (37) will vary depending on the types of decision support functions, feature extraction methods and/or image modalities supported by the respective CAD systems (20) and (30).

Referring now to FIG. 4, a block diagram illustrates a system for providing automated diagnostic and decision support for cardiac imaging according to another exemplary embodiment of the invention. More specifically, FIG. 4 illustrates a multi-modal CAD system (40) that supports automated diagnosis of, e.g., coronary heart disease using image parameters obtained from one or more of various imaging modalities including various ultrasound imaging methods (B-mode, contrast imaging, and/or phase imaging, etc.), MRI, NM, PET, CT, CT angiography, X-ray angiography, MR angiography, etc, and/or non-image patient data, as well as providing other decision support functions to assist physician workflow with regards to one or more cardiac imaging modes. The combination of different imaging modalities can provide various benefits. For example, the different imaging modalities could provide different kinds of information. A nuclear medicine image could provide functional information, such as perfusion, while an ultrasound image could provide anatomical information. Combining these could provide better diagnostic support for the physician. Another example is to combine imaging of coronary arteries with, for example, CT, with information about the left ventricle using ultrasound or MRI. In this way, one could combine information about coronary disease with its effects on the heart muscle.

In one exemplary embodiment, the CAD system (40) of FIG. 4 incorporates some or all of the feature extraction methods, classification methods, diagnostic and decision support methods, etc, of the exemplary CAD systems (10), (20) and (30) as described above. The CAD system (40) of FIG. 4 illustrates one or more exemplary frameworks for the CAD system (10) of FIG. 1 to provide multi-modal CAD for cardiac imaging.

Referring to FIG. 4, the CAD system (40) comprises a data processing system (41) which implements methods to provided automated classification (diagnosis) of heart disease, as well as other decision support functionalities to assist physician workflow, by extracting and analyzing parameters from various sources of patient information (7), including, for example, one or more different types of image data (e.g., MRI image data (7*a*), ultrasound image data (7*b*), NM image data (7*c*)) and non-image data (e.g., data records comprising catherization laboratory data (7d) and clinical, history and/or physical data (7e)) of the subject patient.

In general, the data processing system (41) comprises a feature extraction module (42), a feature combination module (43), a classification module (44) and a diagnostic/workflow assistance module (45). Moreover, the CAD system (40) comprises user interface (46) which enables user interaction with the CAD system (40) to select one or more functions supported by the diagnostic/workflow assistance module (45) (e.g., providing automated diagnosis and confidence of diagnosis for one or more types of cardiac conditions, determine what additional imaging modalities or features could be obtained and further analyzed to increase the confidence in diagnosis, obtain and display one or more similar patient cases in a repository based on a current set of extracted features, etc.)

The feature extraction module (42) implements "n" feature extraction methods for extracting image parameters (42-1~42-2) from the supported imaging modalities, and other feature or text extraction methods (42-3, 42-4) for extracting parameters from non-image data sources. For instance, the feature extraction module (42) can include methods for extracting and analyzing wall motion and thickening parameters from ultrasound images (or other imaging modalities) to provided automated wall motion analysis functions, and other image parameter extraction methods discussed above with reference to FIGS. 3 and 4 for extracting global and regional image parameters. The feature combination module (43) combines a set of extracted features in a manner that is suitable for input and analysis by the classification module (44). The classification module (44) comprises classification methods (44-1) to analyze the combined extracted parameters using one or more classification models, which are trained/dynamically adapted via model builder (44-2), to provide automatic diagnosis of heart disease and other decision support functions. The CAD system (40) further comprises a repository (47) that maintains a clinical domain knowledge base of information which provides training data used by the model builder (44-2) to build/train classification models used by the classification methods (44-1). A large database of analyzed/labeled cases (48) related to the clinical domain or domains supported by the CAD system (40) can be used to obtain training data that is stored in the repository (47). The clinical domain knowledge in repository (47) can be used by the various methods (42, 43, 44 and 45) of the data processing system (41).

It is to be appreciated that the various modules (42, 43, 44 and 45) in FIG. 4 can implement the same or similar methods as those corresponding modules (22, 23, 24 and 25) of the CAD system (20) of FIG. 2 and/or corresponding modules (32, 33, 34 and 35) of the CAD system (30) of FIG. 3, as described above. However, the various methods, such as the classification and model building methods of the classification module (44), will vary depending on the types of decision support functions, feature extraction methods and/or image modalities supported by the CAD system (40). Moreover, the clinical domain knowledge base (47) is similar to the knowledge bases (27) and (37) of FIGS. 2 and 3, except that the training data in knowledge bases (47) will vary depending on the types of decision support functions, feature extraction methods and/or image modalities supported by the CAD system (40).

Figure 6:
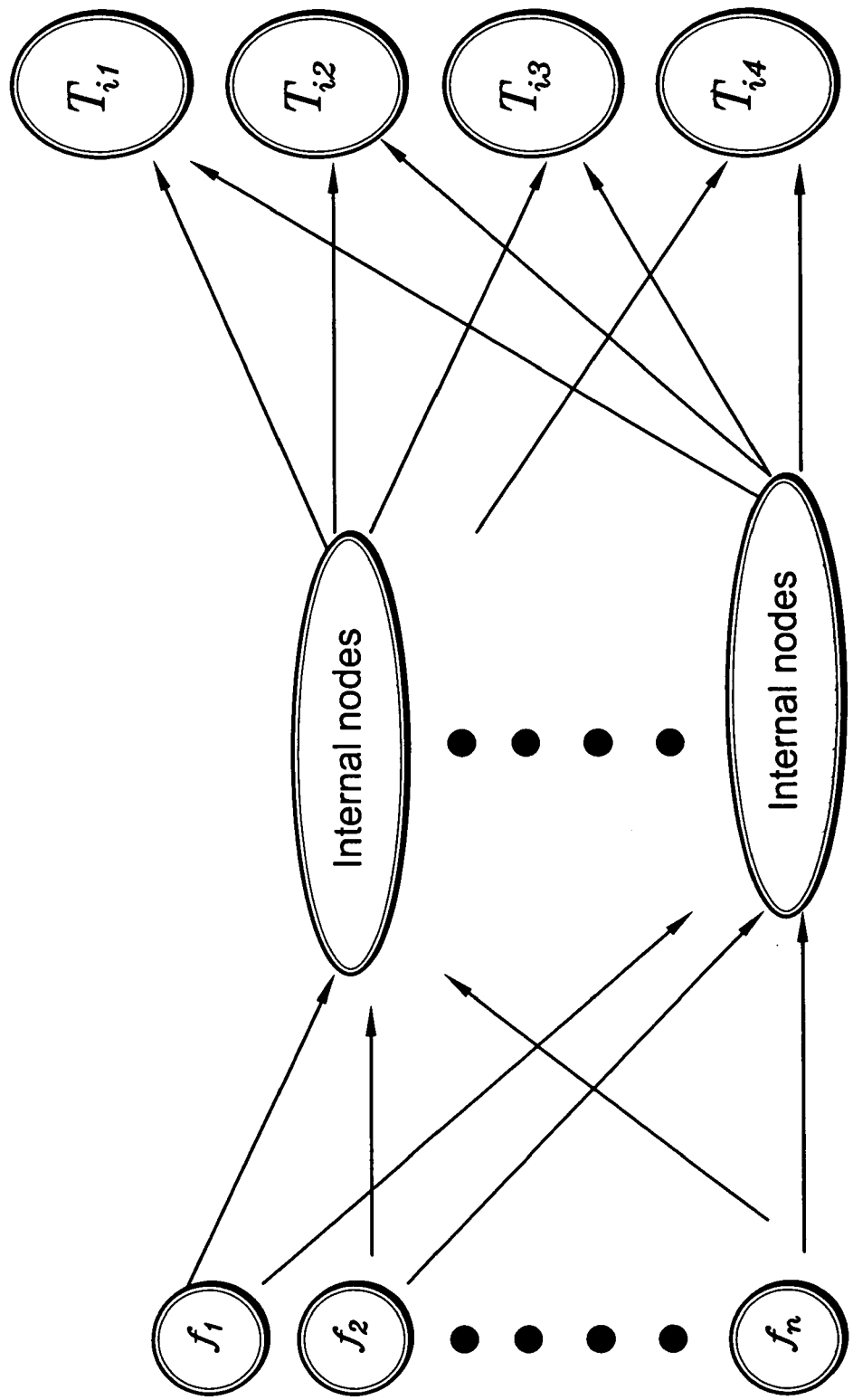
FIG. 6 is an exemplary diagram illustrating a classification method according to an exemplary embodiment of the invention.

Various machine learning methods according to exemplary embodiments of the invention for assessing the likely value of additional tests for diagnosis of cardiac disease, etc., will now be described with reference to the exemplary node diagram of FIG. 6. For these exemplary embodiments, it is assumed that a training set consists of m cases and each case consists of n features extracted from previously performed tests. Each case $C_i$, (i=1, ..., m) can be represented as a vector of features ($f_1, f_2, ..., f_n$).

It is further assumed that for each case $C_i$, the real diagnosis ($d_i$) is:

$$d_i = \begin{cases} 1 & \text{If diagnosis is positive} \\ 0 & \text{Otherwise} \end{cases}$$

and that there are k variables corresponding to the different tests that were performed on the patients ($T_{i1}, T_{i2}, T_{i3}, ..., T_{ik}$), wherein each one of the k variables can take values in the set $\{0,1\}$, and wherein k=1 if the corresponding test predicted correctly with respect to the real diagnosis $d_i$, or where k=0 otherwise.

Further assuming that such previous information is extracted from the training data, the exemplary machine learning based methods described hereafter can be used to predict which test will provide an accurate diagnosis based on a feature vector extracted from a patient medical history.

In one exemplary embodiment, one method is as follows. First, a mapping M is determined from the feature space to $\{(P_1, P_2, P_3, P_4)/P_i \in \{0,1\}\}$ such that for every $C_i$, $M(C_i)=M(f_1, f_2, ..., f_n)=(T_{i1},T_{i2},T_{i3},T_{i4})$. This process can be achieved using artificial neural network techniques as illustrated in FIG. 6. For each new patient, the mapping M will provide a corresponding binary output that describes which tests are recommended for this patient.

This problem also can be viewed as a multi-class classification problem where for each case $C_i$, its label is defined according to which test gave the correct diagnosis. For example, one possible approach is as follows. For each test, all the training cases are labeled according to the accuracy of that test for that case. Then, four classifiers are trained (one for each test) using any binary classification algorithm (e.g., SVMs, Decision Trees, Bayesian networks, etc.). When a new patient is considered, the patient data is tested in the four classifiers to predict which tests will give the correct diagnosis.

It is to be noted that with the above two approaches, the outcome of the process can be more than one test.

Another exemplary approach is as follows. Assume that there are m cases in a training set. A new case will be compared to these m cases using the n features described above. Based on this comparison, p cases are selected as being most "similar" to the current case, wherein similarity can be defined in one of various ways. For instance, one approach is to consider the Euclidean distance in the n-dimensional feature space. Other well-known distance measures can also be employed. It is to be appreciated that the above process can also be used to select exemplar cases from a library of cases for display as well.

One the similarity measures are determined and the most 'similar" cases are identified, classifiers can be constructed for each of the k tests in the training set. In particular, by way of example, a classifier would be constructed to test whether a diagnosis is positive or negative using, for example, each of the following sets of information: (i) current information and results of a wall motion analysis; (ii) current information and ultrasound; (iii) current information and MRI, etc.

Each classifier would be constructed without learning from one of the p cases (i.e. leave-one-out approach), and then the withheld case would be classified using this classifier. This would be repeated for each of the p cases, and the entire process for each of the k tests. An average likelihood would then be computed for each of the k tests, which would serve as the score of which test would be most useful.

It is to be appreciated that in accordance with other exemplary embodiments of the invention, CAD systems may be implemented in a distributed model, wherein various modules/components of the CAD are distributed over a communications network. For example, a CAD system can be offered by an ASP (application service provider) to provide remote access serving of CAD functions via an application server. For example, a database of cases used to identify similar cases could be located in a central location. The advantage is that large databases of cases, which occupy a lot of memory, do not have to reside at every system. In addition, updates to the cases can be made very easily. This central location could be within a hospital, for example, or it could be one central database accessed by everyone using such a system. Another possibility is to use a distributed database, where cases are located in multiple locations but are searched and accessed as if they are in one place. That way, cases located at different locations can be searched to find similar cases. In addition to the database, the other parts of the CAD system, such as the classifier, could be centrally located.

Moreover, in view of above, it is to be appreciated that a CAD system according to the invention can be implemented as a service (e.g., Web service) that is offered by a third-party service provider pursuant to service contract or SLA (service level agreement) to provide diagnostic support and other decision support functions as described herein based one of various service/payment schemes. For example, the third-party service provider can be contractually obligated to train, maintain, and update classification models for various clinical domains, and a physician or healthcare organization can access the CAD system "on-line" on a pay-per use basis, yearly subscription fee, etc. In such instance, various methods known to those of ordinary skill in the art can be implemented to maintain patient confidentiality and otherwise transmit patient data over communication channels using secured encryption, compression schemes, etc. Those of ordinary skill in the art can readily envision various architectures and implementation for CAD systems according to the invention and nothing herein shall be construed as a limitation of the scope of the invention.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method for providing automatic diagnosis and decision support for cardiac imaging, comprising:
   obtaining information from image data of a heart of a patient including a myocardial wall;
   obtaining information from non-image data records of the patient;
   dividing the image data of the myocardial wall into a plurality of segments;
   automatically classifying a condition of the heart using the obtained information and by using a machine learning method, wherein classifying the condition of the heart includes performing a wall motion analysis of the myocardial wall for each of the plurality of segments;
   automatically determining one or more suggested courses of treatment based on the classified condition of the heart;
   automatically determining a probability of success for each of the suggested courses of treatment; and
   presenting the classified condition, the one or more suggested courses of treatment, and the determined probabilities of success to a user as diagnosis and decision support, wherein the classified condition includes a wall motion score for each of the plurality of myocardial wall segments.

2. The method of claim 1, wherein obtaining information from image data comprises automatically extracting one or more features from ultrasound image data in one or more ultrasound imaging modalities.

3. The method of claim 2, wherein the ultrasound image data comprises 3D ultrasound image data.

4. The method of claim 2, wherein automatically extracting one or more features from ultrasound image data comprises extracting global features of heart function, including left ventricular volume, left ventricular ejection fraction, left ventricular wall thickness, left ventricular wall mass, or diastolic function indicators such as the E/A ratio, or any combination of said global features.

5. The method of claim 2, wherein automatically extracting one or more features from ultrasound image data comprises extracting regional parameters, including tissue velocity data, strain data, strain rate data, perfusion data, or timing data, or any combination of said regional parameters.

6. The method of claim 5, wherein automatically extracting one or more features from ultrasound image data comprises extracting features related to strain, fluid motion such as acoustic streaming, blood motion such as contrast perfusion, or B-mode images, or any combination thereof.

7. The method of claim 1, wherein the image data comprises one of ultrasound image data, MR (magnetic resonance) image data, CT (computed tomography) image data, PET image data, nuclear medicine image data, or image data of a coronary artery tree, or any combination thereof.

8. The method of claim 1, wherein obtaining information from non-image data records comprises automatically extracting features from structured and/or unstructured data sources comprising clinical, family and/or history information for the subject patient.

9. The method of claim 1, wherein performing the wall motion analysis comprises automatically extracting image features related to myocardial wall motion and myocardial wall thickening from the image data.

10. The method of claim 1, wherein automatically classifying a condition of the heart comprises automatically assessing a condition of the heart.

11. The method of claim 10, wherein automatically assessing the condition of the heart comprises automatically determining a probability of diagnosis of a heart disease or condition.

12. The method of claim 1, further comprising automatically determining additional information which would increase the confidence value for the classification of the condition of the heart.

13. The method of claim 12, wherein automatically determining additional information further comprises determining a measure of usefulness of said additional information in increasing the confidence value of the classification of the condition of the heart.

14. The method of claim 1, further comprising automatically identifying one or more previous cases that are similar to a current classification.

15. The method of claim 14, wherein automatically identifying one or more previous cases that are similar to a current classification comprises using the obtained information to search a library of labeled cases with features similar to the obtained information.

16. The method of claim 15, comprising displaying the identified cases.

17. The method of claim 1, wherein automatically classifying a condition of the heart additionally uses a model-based method.

18. The method of claim 1, additionally comprising retraining the machine learning method on a continual or periodic basis using expert data and/or data learned from a plurality of case studies.

19. A method for providing automated diagnostic and decision support for cardiac imaging, comprising:
    automatically extracting features from patient data of a subject patient, the patient data comprising image data including a myocardial wall and non-image data;
    automatically dividing the image data of the myocardial wall into a plurality of segments;
    automatically determining a current state of a heart of the subject patient by analyzing the features extracted from the patient data of the subject patient and by using a machine learning method, wherein determining the current state of the heard includes performing a wall motion analysis of the myocardial wall for each of the plurality of segments;
    automatically determining one or more suggested courses of treatment based on the determined current state of the heart;
    automatically determining a probability of success for each of the suggested courses of treatment;
    automatically providing decision support to assist physician workflow regarding a healthcare or diagnostic or therapeutic path for the subject patient, based on a determined current state of the subject patient; and
    presenting the classified condition, the one or more suggested courses of treatment, and the determined probabilities of success to a user as diagnosis and decision support, wherein the classified condition includes a wall motion score for each of the plurality of myocardial wall segments.

20. The method of claim 19, wherein automatically determining a current state of the subject patient comprises automatically determining a probability of diagnosis of a heart disease or condition or the probability of developing a heart disease or condition in the future.

21. The method of claim 20, wherein automatically providing decision support comprises automatically determining one or more additional features of patient which would increase a confidence of said probability of diagnosis.

22. The method of claim 21, wherein automatically determining one or more additional features further comprises determining for each of said one or more additional features, a measure of usefulness in increasing said confidence of diagnosis.

23. The method of claim 20, wherein automatically providing decision support comprises automatically determining one or more additional cardiac imaging tests which would increase a confidence of said probability of diagnosis.

24. The method of claim 23, wherein automatically determining one or more additional cardiac imaging tests further comprises determining for each of said one or more additional tests, a measure of usefulness in increasing said confidence of diagnosis.

25. The method of claim 20, wherein automatically providing decision support comprises automatically identifying one or more previously diagnosed cases that are similar to the current case.

26. The method of claim 25, comprising displaying the one or more identified similar cases.

27. The method of claim 19, wherein automatically determining a current state of the subject patient comprises automatically determining a likelihood of the subject patient developing a heart disease or condition.

28. The method of claim 19, further comprising automatically providing a measure of confidence that each of the suggested courses of treatment will have a determined outcome.

29. The method of claim 19, further comprising automatically providing a probability and/or measure of confidence that each of the suggested courses of treatment will not have a determined detrimental impact such as side effects.

30. The method of claim 19, wherein the probability of success for each of the suggested courses of treatment is a distribution over possible outcomes both beneficial and detrimental.

31. The method of claim 19, wherein the probability of success for each of the suggested courses of treatment is a set of distributions over possible outcomes both beneficial and detrimental at one or more time points in the future.

32. The method of claim 19, wherein the probability of success for each of the suggested courses of treatment is a time-varying distribution over possible outcomes at different times in the future.

33. A method for providing automatic diagnosis and decision support for cardiac imaging, comprising:
    obtaining information from image data of a heart of a patient from at least two different imaging modalities, including ultrasound, MR, CT, PET, MR angiography, CT angiography, X-ray angiography, and nuclear medicine, the image data of the heard including a myocardial wall;
    dividing the image data of the at least two imaging modalities of the myocardial wall into a plurality of segments;
    extracting features from the image data of the at least two imaging modalities, and automatically determining a current state of the patient by analyzing the extracted features and by using a machine learning method, wherein determining the current state of the patient includes performing a wall motion analysis of the myocardial wall for each of the plurality of segments;
    automatically determining one or more suggested courses of treatment based on the determined current state of the patient;
    automatically determining a probability of success for each of the suggested courses of treatment; and
    automatically providing decision support to assist physician workflow regarding a healthcare or diagnostic or therapeutic path for the patient, based on a determined current state of the subject patient, the one or more suggested courses of treatment, and the automatically determined probabilities of success, wherein the determined current state of the subject patient includes a wall motion score for each of the plurality of myocardial wall segments.

34. The method of claim 33, where the extracted features from the image data are combined with features from non-imaging data of the patient.

35. The method of claim 19, where one of the imaging modalities is used to image coronary arteries.

36. The method of claim 35, wherein CT angiography is used to extract features on coronary arteries, and one or more of CT, MR, PET, nuclear medicine, and ultrasound is used to image the myocardium of the heart.

37. The method of claim 35, wherein MR angiography is used to extract features on coronary arteries, and one or more of CT, MR, PET, nuclear medicine, and ultrasound is used to image the myocardium of the heart.

38. The method of claim 35, wherein X-ray angiography is used to extract features on coronary arteries, and one or more of CT, MR, PET, nuclear medicine, and ultrasound is used to image the myocardium of the heart.

* * * * *